(12) United States Patent
Brockway et al.

(10) Patent No.: US 7,668,594 B2
(45) Date of Patent: Feb. 23, 2010

(54) METHOD AND APPARATUS FOR DELIVERING CHRONIC AND POST-ISCHEMIA CARDIAC THERAPIES

(75) Inventors: Marina Brockway, Shoreview, MN (US); Joseph M. Pastore, Woodbury, MN (US); Yi Zhang, Blaine, MN (US); Carlos Ricci, Apple Valley, MN (US); Allan Shuros, St. Paul, MN (US); Rodney W. Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 552 days.

(21) Appl. No.: 11/207,251

(22) Filed: Aug. 19, 2005

(65) Prior Publication Data

US 2007/0043393 A1    Feb. 22, 2007

(51) Int. Cl.
  *A61N 1/368*   (2006.01)
  *A61N 1/08*    (2006.01)
(52) U.S. Cl. ............. 607/9; 607/2; 607/3; 607/18
(58) Field of Classification Search .......... 607/3, 607/6, 7, 2, 9, 18, 17; 600/481, 485, 515
  See application file for complete search history.

(56) References Cited

U.S. PATENT DOCUMENTS

| | | | |
|---|---|---|---|
| 3,650,277 A | 3/1972 | Sjostrand et al. | |
| 4,587,975 A | 5/1986 | Salo et al. | |
| 4,730,619 A | 3/1988 | Koning et al. | |
| 4,791,931 A | 12/1988 | Slate | |
| 4,834,710 A | 5/1989 | Fleck | |
| 4,919,133 A | 4/1990 | Chiang | |
| 5,007,427 A | 4/1991 | Suzuki et al. | |
| 5,024,222 A | 6/1991 | Thacker | |
| 5,058,584 A | 10/1991 | Bourgeois | |
| 5,072,458 A | 12/1991 | Suzuki | |
| 5,111,818 A | 5/1992 | Suzuki et al. | |
| 5,135,004 A | 8/1992 | Adams et al. | |
| 5,184,615 A | 2/1993 | Nappholz et al. | |
| 5,199,428 A * | 4/1993 | Obel et al. .............. 607/44 |

(Continued)

FOREIGN PATENT DOCUMENTS

| | | |
|---|---|---|
| EP | 0547734 A2 | 6/1993 |
| EP | 1437159 A1 | 7/2004 |
| WO | WO-95/18649 A1 | 7/1995 |
| WO | WO-01/15609 A1 | 3/2001 |
| WO | WO-0124876 A1 | 4/2001 |

(Continued)

OTHER PUBLICATIONS

"Application No. PCT/US2006/000125, International Search Report and Written Opinion mailed May 11, 2006", 12 pgs.

(Continued)

*Primary Examiner*—Carl H Layno
*Assistant Examiner*—Natasha N Patel
(74) *Attorney, Agent, or Firm*—Schwegman, Lundberg & Woessner, P.A.

(57) ABSTRACT

An implantable cardiac rhythm management (CRM) device delivers a chronic therapy while detecting an ischemic state. When the ischemic state indicates the occurrence of an ischemic event, the implantable CRM device delivers a post-ischemia therapy. The post-ischemia therapy and the chronic therapy are adjusted using feedback control with the ischemic state and parameters indicative of the effectiveness of the post-ischemic therapy and the effectiveness of the chronic therapy as inputs.

25 Claims, 8 Drawing Sheets

U.S. PATENT DOCUMENTS

| | | | |
|---|---|---|---|
| 5,282,840 A | 2/1994 | Hudrlik et al. |
| 5,313,953 A | 5/1994 | Yomtov et al. |
| 5,376,106 A | 12/1994 | Stahmann et al. |
| 5,484,419 A | 1/1996 | Fleck |
| 5,531,768 A | 7/1996 | Alferness |
| 5,588,432 A | 12/1996 | Crowley |
| 5,755,671 A | 5/1998 | Albrecht et al. |
| 5,824,021 A | 10/1998 | Rise |
| 5,919,209 A | 7/1999 | Schouten |
| 6,021,350 A | 2/2000 | Mathson |
| 6,058,331 A | 5/2000 | King |
| 6,104,956 A | 8/2000 | Naritoku et al. |
| 6,108,577 A | 8/2000 | Benser |
| 6,115,628 A * | 9/2000 | Stadler et al. ............... 600/517 |
| 6,233,486 B1 | 5/2001 | Ekwall et al. |
| 6,238,422 B1 | 5/2001 | Oort |
| 6,256,538 B1 | 7/2001 | Ekwall |
| 6,272,379 B1 | 8/2001 | Fischell et al. |
| 6,285,907 B1 | 9/2001 | Kramer et al. |
| 6,314,323 B1 * | 11/2001 | Ekwall ........................ 607/23 |
| 6,368,284 B1 | 4/2002 | Bardy |
| 6,408,208 B1 | 6/2002 | Sun |
| 6,411,845 B1 | 6/2002 | Mower |
| 6,445,953 B1 | 9/2002 | Bulkes et al. |
| 6,477,402 B1 | 11/2002 | Lynch et al. |
| 6,569,145 B1 | 5/2003 | Shmulewitz et al. |
| 6,584,362 B1 | 6/2003 | Scheiner et al. |
| 6,604,000 B2 | 8/2003 | Lu |
| 6,610,713 B2 | 8/2003 | Tracey |
| 6,628,988 B2 | 9/2003 | Kramer et al. |
| 6,711,436 B1 | 3/2004 | Duhaylongsod |
| 6,763,267 B2 | 7/2004 | Ding |
| 6,827,690 B2 | 12/2004 | Bardy |
| 6,838,471 B2 | 1/2005 | Tracey |
| 6,842,642 B2 | 1/2005 | Vanhout |
| 6,845,267 B2 | 1/2005 | Harrison et al. |
| 6,865,420 B1 | 3/2005 | Kroll |
| 6,892,095 B2 | 5/2005 | Salo |
| 6,907,285 B2 | 6/2005 | Denker et al. |
| 6,913,577 B2 | 7/2005 | Bardy |
| 6,937,899 B2 * | 8/2005 | Sheldon et al. ............... 607/18 |
| 6,950,701 B2 | 9/2005 | Begemann et al. |
| 6,965,797 B2 | 11/2005 | Pastore et al. |
| 6,973,349 B2 * | 12/2005 | Salo ............................ 607/11 |
| 7,010,345 B2 | 3/2006 | Hill et al. |
| 7,025,730 B2 | 4/2006 | Cho et al. |
| 7,039,462 B2 | 5/2006 | Pastore et al. |
| 7,062,314 B2 | 6/2006 | Zhu et al. |
| 7,062,325 B1 | 6/2006 | Krig et al. |
| 7,069,070 B2 | 6/2006 | Carlson et al. |
| 7,072,711 B2 | 7/2006 | Girouard et al. |
| 7,092,755 B2 | 8/2006 | Florio |
| 7,158,832 B2 | 1/2007 | Kieval et al. |
| 7,171,258 B2 | 1/2007 | Goode |
| 7,215,992 B2 | 5/2007 | Stahmann et al. |
| 7,215,997 B2 | 5/2007 | Yu et al. |
| 7,277,761 B2 | 10/2007 | Shelchuk |
| 7,295,874 B2 | 11/2007 | Prinzen et al. |
| 7,299,087 B2 | 11/2007 | Bardy |
| 7,333,854 B1 | 2/2008 | Brewer et al. |
| 7,340,303 B2 | 3/2008 | Zhu |
| 7,364,547 B2 | 4/2008 | Stahmann et al. |
| 7,366,568 B2 | 4/2008 | Pastore et al. |
| 7,460,906 B2 | 12/2008 | Libbus |
| 7,479,112 B2 | 1/2009 | Sweeney et al. |
| 7,486,991 B2 | 2/2009 | Libbus et al. |
| 2002/0026222 A1 | 2/2002 | Schauerte et al. |
| 2002/0042632 A1 | 4/2002 | Iaizzo et al. |
| 2002/0072776 A1 | 6/2002 | Osorio et al. |
| 2002/0072777 A1 | 6/2002 | Lu |
| 2002/0082660 A1 | 6/2002 | Stahmann et al. |
| 2002/0091415 A1 | 7/2002 | Lovett et al. |
| 2002/0123772 A1 | 9/2002 | Sun et al. |
| 2002/0128563 A1 | 9/2002 | Carlson et al. |
| 2003/0004549 A1 | 1/2003 | Hill et al. |
| 2003/0009189 A1 | 1/2003 | Gilson et al. |
| 2003/0045908 A1 | 3/2003 | Condie et al. |
| 2003/0060854 A1 | 3/2003 | Zhu |
| 2003/0105493 A1 | 6/2003 | Salo |
| 2003/0120313 A1 | 6/2003 | Begemann et al. |
| 2003/0120315 A1 | 6/2003 | Spinelli et al. |
| 2003/0139778 A1 | 7/2003 | Fischell et al. |
| 2003/0158584 A1 | 8/2003 | Cates et al. |
| 2003/0199956 A1 | 10/2003 | Struble et al. |
| 2003/0204206 A1 | 10/2003 | Padua et al. |
| 2003/0204231 A1 | 10/2003 | Hine et al. |
| 2003/0229380 A1 | 12/2003 | Adams et al. |
| 2003/0233130 A1 | 12/2003 | Padmanabhan et al. |
| 2004/0015081 A1 | 1/2004 | Kramer et al. |
| 2004/0038947 A1 | 2/2004 | Wink et al. |
| 2004/0088015 A1 | 5/2004 | Casavant et al. |
| 2004/0088017 A1 | 5/2004 | Sharma et al. |
| 2004/0102815 A1 | 5/2004 | Balczewski et al. |
| 2004/0106960 A1 | 6/2004 | Siejko et al. |
| 2004/0106961 A1 | 6/2004 | Siejko et al. |
| 2004/0133247 A1 | 7/2004 | Stahmann et al. |
| 2004/0230240 A1 | 11/2004 | Sun et al. |
| 2004/0255956 A1 | 12/2004 | Vinten-Johansen et al. |
| 2005/0004476 A1 | 1/2005 | Payvar et al. |
| 2005/0038345 A1 | 2/2005 | Gorgenberg et al. |
| 2005/0043675 A1 | 2/2005 | Pastore et al. |
| 2005/0075673 A1 | 4/2005 | Warkentin et al. |
| 2005/0090719 A1 | 4/2005 | Scheiner et al. |
| 2005/0096705 A1 | 5/2005 | Pastore et al. |
| 2005/0096706 A1 | 5/2005 | Salo |
| 2005/0131467 A1 | 6/2005 | Boveja |
| 2005/0137631 A1 | 6/2005 | Yu et al. |
| 2005/0143779 A1 | 6/2005 | Libbus |
| 2005/0149126 A1 | 7/2005 | Libbus |
| 2005/0149127 A1 | 7/2005 | Libbus |
| 2005/0149129 A1 | 7/2005 | Libbus et al. |
| 2005/0171589 A1 | 8/2005 | Lau et al. |
| 2005/0197674 A1 | 9/2005 | McCabe et al. |
| 2005/0261741 A1 | 11/2005 | Libbus et al. |
| 2005/0283195 A1 | 12/2005 | Pastore et al. |
| 2005/0288721 A1 | 12/2005 | Girouard et al. |
| 2006/0030892 A1 | 2/2006 | Kadhiresan et al. |
| 2006/0116593 A1 | 6/2006 | Zhang et al. |
| 2006/0136049 A1 | 6/2006 | Rojo |
| 2006/0149326 A1 | 7/2006 | Prinzen et al. |
| 2006/0195038 A1 | 8/2006 | Carlson et al. |
| 2006/0206158 A1 | 9/2006 | Wu et al. |
| 2006/0241704 A1 | 10/2006 | Shuros et al. |
| 2006/0247686 A1 | 11/2006 | Girouard et al. |
| 2006/0247700 A1 | 11/2006 | Jackson |
| 2006/0253156 A1 | 11/2006 | Pastore et al. |
| 2006/0259087 A1 | 11/2006 | Baynham et al. |
| 2006/0259088 A1 | 11/2006 | Pastore et al. |
| 2006/0282000 A1 | 12/2006 | Zhang et al. |
| 2006/0287684 A1 | 12/2006 | Baynham et al. |
| 2007/0021789 A1 | 1/2007 | Pastore et al. |
| 2007/0021790 A1 | 1/2007 | Kieval et al. |
| 2007/0021798 A1 | 1/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0049835 A1 | 3/2007 | Goode |
| 2007/0054871 A1 | 3/2007 | Pastore et al. |
| 2007/0060972 A1 | 3/2007 | Kieval et al. |
| 2007/0142864 A1 | 6/2007 | Libbus et al. |
| 2007/0142871 A1 | 6/2007 | Libbus et al. |
| 2007/0150005 A1 | 6/2007 | Sih et al. |
| 2007/0150015 A1 | 6/2007 | Zhang et al. |
| 2007/0162081 A1 | 7/2007 | Yu et al. |

| | | | |
|---|---|---|---|
| 2007/0167984 A1 | 7/2007 | Kieval et al. | |
| 2007/0179392 A1 | 8/2007 | Zhang | |
| 2007/0239218 A1 | 10/2007 | Carlson et al. | |
| 2007/0282380 A1 | 12/2007 | Brooke et al. | |
| 2007/0299356 A1 | 12/2007 | Wariar et al. | |
| 2008/0015659 A1 | 1/2008 | Zhang et al. | |
| 2008/0021507 A1 | 1/2008 | Libbus et al. | |
| 2008/0027495 A1 | 1/2008 | Prinzen et al. | |
| 2008/0058661 A1 | 3/2008 | Bardy | |
| 2008/0058881 A1 | 3/2008 | Wagner et al. | |
| 2008/0081354 A1 | 4/2008 | Qu et al. | |
| 2008/0082135 A1 | 4/2008 | Arcot et al. | |
| 2008/0091138 A1 | 4/2008 | Pastore et al. | |
| 2008/0132972 A1 | 6/2008 | Shuros et al. | |
| 2008/0140141 A1 | 6/2008 | Ben-David et al. | |
| 2008/0167694 A1 | 7/2008 | Bolea et al. | |
| 2008/0177156 A1 | 7/2008 | Zhang et al. | |
| 2008/0177191 A1 | 7/2008 | Patangay et al. | |
| 2008/0177194 A1 | 7/2008 | Zhang et al. | |
| 2008/0215105 A1 | 9/2008 | Pastore et al. | |
| 2009/0025459 A1 | 1/2009 | Zhang et al. | |
| 2009/0048641 A1 | 2/2009 | Libbus | |
| 2009/0082781 A1 | 3/2009 | Tran et al. | |
| 2009/0124916 A1 | 5/2009 | Sweeney et al. | |
| 2009/0192560 A1 | 7/2009 | Arcot-Krishnamurthy et al. | |

FOREIGN PATENT DOCUMENTS

| | | | |
|---|---|---|---|
| WO | WO-0128625 A1 | 4/2001 | |
| WO | WO-0176689 A2 | 10/2001 | |
| WO | WO-03082080 A2 | 10/2003 | |
| WO | WO-2004/058326 A2 | 7/2004 | |
| WO | WO-2005042091 A1 | 5/2005 | |
| WO | WO-2006/074189 A1 | 7/2006 | |
| WO | WO-2006/079010 A1 | 7/2006 | |
| WO | WO-2006/115693 A2 | 11/2006 | |
| WO | WO-2006/121842 A1 | 11/2006 | |
| WO | WO-2006/124636 A2 | 11/2006 | |
| WO | WO-2006/124729 A2 | 11/2006 | |
| WO | WO-2006115693 A3 | 11/2006 | |
| WO | WO-2007078410 A1 | 7/2007 | |
| WO | WO-2007/133962 A2 | 11/2007 | |
| WO | WO-2008063396 A1 | 5/2008 | |

OTHER PUBLICATIONS

"U.S. Appl. No. 11/030,575, Non Final Office Action mailed Jul. 26, 2006", 11 pgs.

"U.S. Appl. No. 11/030,575 Response filed Oct. 26, 2006 to Non Final Office Action mailed Jul. 26, 2006", 8 pgs.

"U.S. Appl. No. 11/129,050, Non-Final Office Action mailed Nov. 26, 2007", 7 pgs.

"U.S. Appl. No. 11/129,050, Response filed Feb. 26, 2008 to Non-Final Office Action mailed Nov. 26, 2007", 14 pgs.

"U.S. Appl. No. 11/129,050, Response filed Sep. 28, 2007 to Restriction Requirement mailed Aug. 1, 2007", 11 pgs.

"U.S. Appl. No. 11/151,015, Non Final Office Action mailed May 21, 2007", 14 pgs.

"U.S. Appl. No. 11/151,015, Response filed Aug. 21, 2007 to Non-Final Office Action mailed May 21, 2007", 9 pages.

"PCT Application No. PCT/US2006/017384, International Search Report and Written Opinion mailed Jan. 23, 2007", 12 pgs.

"PCT Application No. PCT/US2006/018642, International Search Report and Written Opinion mailed Oct. 24, 2006", 14 pgs.

"PCT Application No. PCT/US2007/068217, International Search Report mailed Oct. 30, 2007", 5 pgs.

"PCT Application No. PCT/US2007/068217, Written Opinion mailed Oct. 30, 2007", 8 pgs.

Kis, A., "Repeated Cardiac Pacing Extends the Time During Which Canine Hearts are Protected Against Ischaemia-Induced Arrhythmias: Role of Nitric Oxide.", *Journal of Molecular and Cellular Cardiology*, 31(6), (1999), 1229-1241.

Kloner, R. A., et al., "Prospective Temporal Analysis of the Onset of Preinfarction Angina Versus Outcome: An Ancillary Study in TIMI-9B", *Circulation*, 97(11), (1998), 1042-1045.

Koning, M. M. G.., "Rapid Ventricular Pacing Produces Myocardial Protection by Nonischemic Activation of $K_{ATP}^+$ Channels", *Circulation*, 93(1), (1996),178-186.

Loukogeorgakis, S. P., et al., "Remote Ischemic Preconditioning Provides Early and Late Protection Against Endothelial Ischemia-Reperfusion Injury in Humans: Role of the Autonomic Nervous System.", *Journal of the American College of Cardiology* 46(3), (2005), 450-456.

Meier, B., et al., "Coronary Pacing During Percutaneous Transluminal Coronary Angioplasty", *Therapy And Prevention Cardiac Pacing*, 71(3), (1985), 557-561.

Murry, C. E., "Preconditioning with Ischemia: a Delay of Lethal Cell Injury in Ischemic Myocardium", *Circulation*, 74(5), (1986), 1124-1136.

Ovize, M., et al., "Stretch Preconditions Canine Myocardium.", *Am J Physiol.*, 266(1 Pt 2), (1994), H137-H146.

Rosa, A., et al., "Ectopic Pacing at Physiological Rate Improves Postanoxic Recovery of the Developing Heart", *Am. J. Physiol.—Heart Circ. Physiol.*, 284, (2003), H2384-H2392.

Tsang, A., et al., "Postconditioning: a Form of "Modified Reperfusion" Protects the Myocardium by Activating the Phosphatidylinositol 3-Kinase-Akt Pathway", *Circ Res.*, 95(3), (2004), 230-232.

Vanagt, W. Y., et al., "Ventricular Pacing for Improving Myocardial Tolerance to Ischemia, Progress Report on Project Guidant-CARIM", (Oct. 2003), 25 pgs.

Vegh, A., et al., "Transient Ischaemia Induced by Rapid Cardiac Pacing Results in Myocardial Preconditioning", *Cardiovascular Research*, 25(12), (Dec. 1991), 1051-1053.

Wu, Z.-K., et al., "Ischemic Preconditioning Suppresses Ventricular Tachyarrhythmias After Myocardial Revascularization", *Circulation*, 106(24), (2002), 3091-3096.

Yang, S. M., et al.,"Multiple, Brief Coronary Occlusions During Early Reperfusion Protect Rabbit Hearts by Targeting Cell Signaling Pathways", *Journal of the American College of Cardiology*, 44(5), (2004), 1103-1110.

Zhao, Z.-Q. , et al., "Inhibition of Myocardial Injury by Ischemic Postconditioning During Reperfusion: Comparison with Ischemic Preconditioning", *Am J Physiol Heart Circ Physiol*, 285(2), (2003), H579-H588.

"U.S. Appl. No. 11/129,050, Advisory Action mailed Jul. 28, 2008", 3 pgs.

"U.S. Appl. No. 11/129,050, Final Office Action mailed May 12, 2008", 8 pgs.

"U.S. Appl. No. 11/129,050, Response filed Jul. 14, 2008 to Final Office Action mailed May 12, 2008", 13 pgs.

"U.S. Appl. No. 11/129,050 Response filed Sep. 12, 2008 to Final Office Action mailed May 12, 2008 and Advisory Action mailed Jul. 28, 2008", 12 pages.

"U.S. Appl. No. 11/129,058, Advisory Action mailed Oct. 17, 2007", 3 pgs.

"U.S. Appl. No. 11/129,058, Appeal Brief filed Jan. 8, 2008", 22 pgs.

"U.S. Appl. No. 11/129,058, Examiner's Answer mailed Jun. 18, 2008", 14 pgs.

"U.S. Appl. No. 11/318,263, Non-Final Office Action mailed Aug. 20, 2008", 10 pgs.

Andersen, H, "Long-term follow-up of patients from a randomised trial of atrial versus ventricular pacing for sick-sinus syndrome", *Lancet*, 350(9086), (Oct. 25, 1997), 1210-6.

Benchimol, A, "Cardiac hemodynamics during stimulation of the right atrium, right ventricle, and left ventricle in normal and abnormal hearts", *Circulation*, 33(6), (Jun. 1966), 933-44.

Grassi, Guido, et al., "Baroreflex and non-baroreflex modulation of vagal cardiac control after myocardial infarction", *Am J Cardiol.*, 84(5), (Sep. 1, 1999), 525-9.

Leclercq, C, et al., "Hemodynamic importance of preserving the normal sequence of ventricular activation in permanent cardiac pacing", *Am Heart J.*, 129(6), (Jun. 1995), 1133-41.

Rosenqvist, M, "The effect of ventricular activation sequence on cardiac performance during pacing", *Pacing and Electrophysiology*, 19(9), (1996), 1279-1286.

"U.S. Appl. No. 11/129,080, Response filed Feb. 23, 2009 to Non Final Office Action mailed Nov. 6, 2008", 13 pgs.

"U.S. Appl. No. 11/129,050 Non-Final Office Action mailed Nov. 6, 2008", 8 pgs.

"U.S. Appl. No. 11/318,263, Response filed Nov. 20, 2008 to Non Final Office Action mailed Aug. 20, 2008", 12 pgs.

"U.S. Appl. No. 11/318,263, Final Office Action mailed Mar. 17, 2009", 12 pgs.

"U.S. Appl. No. 11/113,828, Non-Final Office Action mailed Mar. 5, 2008", 8 pgs, 9 pgs.

07797336.0, "European Application Serial No. 07797336.0, Office Action mailed Feb. 24, 2009", 4 pgs.

"U.S. Appl. No. 11/129,050, Notice of Allowance mailed Aug. 24, 2009", 9 Pgs.

"U.S. Appl. No. 11/318,263, Response filed Aug. 12, 2009 to Restriction Requirement mailed Jul. 14, 2009", 9 pgs.

\* cited by examiner

METHOD AND APPARATUS FOR DELIVERING CHRONIC AND POST-ISCHEMIA CARDIAC THERAPIES

CROSS-REFERENCE TO RELATED APPLICATIONS

This application is related to, commonly assigned, U.S. patent application Ser. No. 11/129,058, entitled "METHOD AND APPARATUS FOR DELIVERING PACING PULSES USING A CORONARY STENT," filed on May 13, 2005 and U.S. patent application Ser. No. 11/129,050, entitled "METHOD AND APPARATUS FOR CARDIAC PROTECTION PACING," filed on May 13, 2005, which are incorporated herein by reference in their entirety.

TECHNICAL FIELD

This document relates generally to cardiac rhythm management (CRM) systems and particularly, but not by way of limitation, to a system that delivers chronic and post-ischemia cardiac therapies.

BACKGROUND

The heart is the center of a person's circulatory system. It includes an electro-mechanical system performing two major pumping functions. The left portions of the heart, including the left atrium (LA) and the left ventricle (LV), draw oxygenated blood from the lungs and pump it to the organs of the body to provide the organs with their metabolic needs for oxygen. The right portions of the heart, including the right atrium (RA) and the right ventricle (RV), draw deoxygenated blood from the body organs and pump it to the lungs where the blood gets oxygenated. These pumping functions are resulted from contractions of the myocardium. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system cause the various portions of the heart to contract in synchrony to result in efficient pumping functions. A blocked or otherwise abnormal electrical conduction and/or deteriorated myocardial tissue cause dysynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen and metabolite removal due to an interruption in blood supply caused by an occlusion of a blood vessel such as a coronary artery. The necrotic tissue, known as infarcted tissue, loses the contractile properties of the normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance, higher risk of ventricular arrhythmia, and a significantly increased risk of developing heart failure.

Therefore, there is a need to improve cardiac function and control remodeling following ischemic events, including MI. For a patient who has been receiving a cardiac therapy on a long-term basis prior to the occurrence of such an ischemic event, there is a need to adjust the therapeutic strategy in response to the ischemic event.

SUMMARY

An implantable CRM device delivers a chronic therapy while detecting an ischemic state. When the ischemic state indicates the occurrence of an ischemic event, the implantable CRM device delivers a post-ischemia therapy. The post-ischemia therapy and the chronic therapy are adjusted using feedback control with the ischemic state and parameters indicative of the effectiveness of the post-ischemic therapy and the effectiveness of the chronic therapy as inputs.

In one embodiment, a CRM system includes a sensing circuit, an ischemia detector, a therapy delivery device, a therapy monitor, and a controller. The sensing circuit senses one or more physiological signals including one or more ischemia-indicating signals and one or more therapy-monitoring signals. The ischemia detector detects an ischemic state indicative of an occurrence of an ischemic event from the one or more ischemia-indicating signals. The therapy delivery device delivers a post-ischemia therapy and a chronic therapy. The therapy monitor produces one or more therapy-monitoring parameters from the one or more therapy-monitoring signals. The one or more therapy-monitoring parameters each indicate effectiveness of at least one of the post-ischemia therapy and the chronic therapy. The controller includes a post-ischemia therapy controller and a chronic therapy controller. The post-ischemia therapy controller initiates the delivery of the post-ischemia therapy and adjusts the delivery of the post-ischemia therapy based on the detected ischemic state and at least one post-ischemia therapy-monitoring parameter of the one or more therapy-monitoring parameters. The chronic therapy controller adjusts the delivery of the chronic therapy based on the detected ischemic state and at least one chronic therapy-monitoring parameter of the one or more therapy-monitoring parameters.

In one embodiment, a method for treating a heart with an ischemic region is provided. A chronic therapy is delivered. One or more physiological signals are sensed. The one or more physiological signals include one or more ischemia-indicating signals and one or more therapy-monitoring parameters. An ischemic state indicative of an occurrence of an ischemic event is detected from the one or more ischemia-indicating signals. A delivery of a post-ischemia therapy is initiated in response to the occurrence of the ischemic event as indicated by the detected ischemic state. One or more therapy-monitoring parameters are produced from the one or more therapy-monitoring signals. The one or more therapy-monitoring parameters each indicate effectiveness of at least one of the chronic therapy and the post-ischemia therapy. The delivery of the chronic therapy and the delivery of the post-ischemia therapy are adjusted based on the detected ischemic state and the one or more therapy-monitoring parameters.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof.

The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses an implantable medical device that includes a pacing and post-ischemia therapy system. In various embodiments, the pacing and post-ischemia therapy system provides a patient with a long-term cardiac therapy and a post-ischemia cardiac therapy. The implantable medical device delivers a chronic (long-term) pacing therapy. Examples of such chronic pacing therapy include bradycardia pacing therapy, cardiac resynchronization therapy (CRT), and cardiac remodeling control therapy (RCT). The implantable medical device includes a real-time ischemia detector that detects an ischemic state of the patient. The ischemic state indicates occurrences of ischemic event such as acute MI. In response to the occurrence of an ischemic event, the implantable medical device delivers a post-ischemia therapy and, if necessary, adjusts the chronic pacing therapy. The post-ischemia therapy controls or minimizes the damage to the myocardium associated with the ischemic event. Examples of the post-ischemia therapy include post-ischemia pacing therapy, neural stimulation therapy, drug therapy, and biological therapy. A controller of the pacing and post-ischemia therapy system provides for adjustment of the chronic pacing therapy and the post-ischemia therapy by feedback control using one or more sensed physiological signals as inputs.

Figure 1:
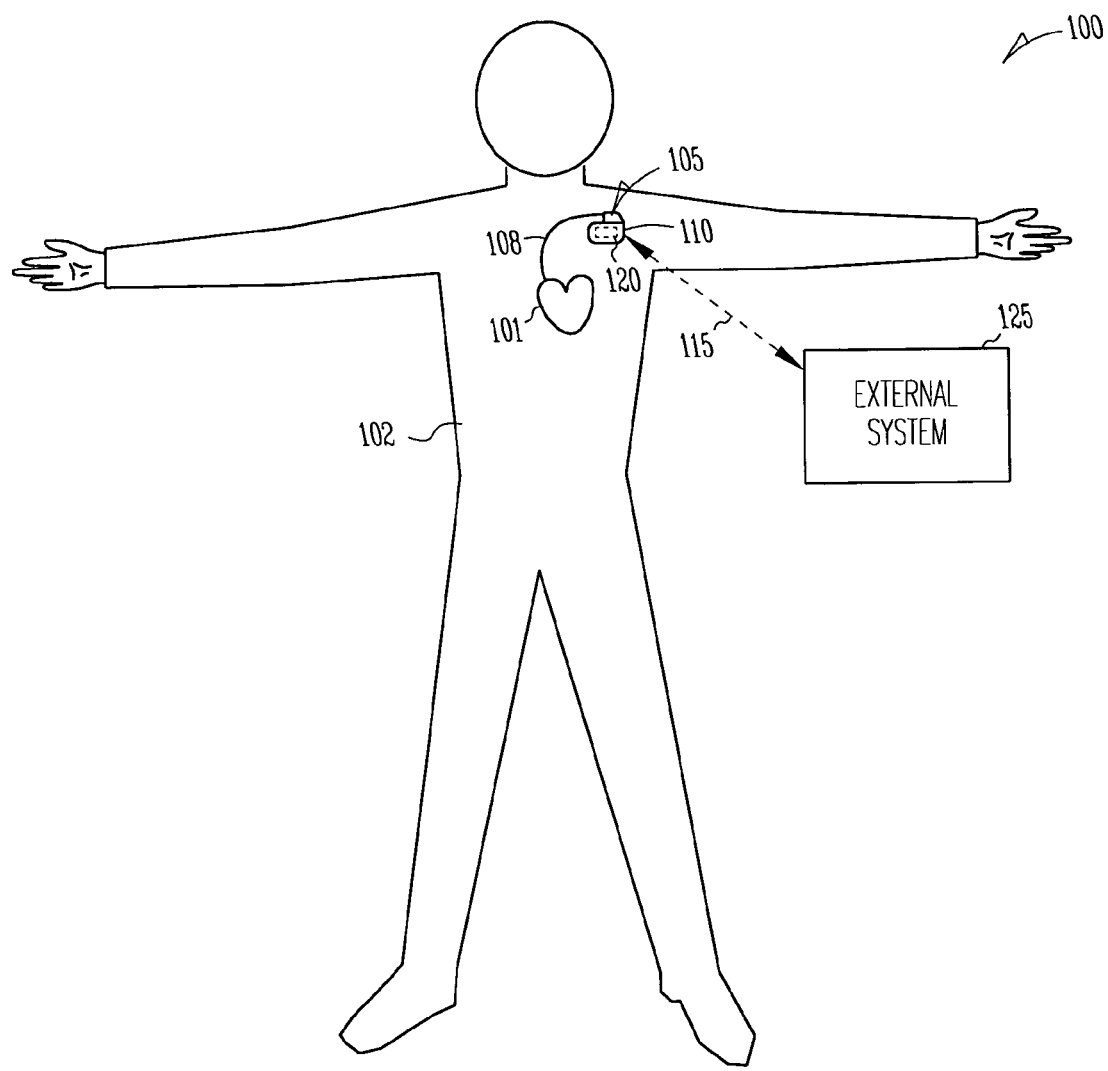
FIG. 1 is an illustration of an embodiment of a CRM system including an implantable system and an external system and portions of an environment in which the CRM system is used.

FIG. 1 is an illustration of an embodiment of a CRM system 100 and portions of an environment in which system 100 is used. System 100 includes an implantable system 105, an external system 125, and a telemetry link 115 providing for communication between implantable system 105 and external system 125.

Implantable system 105 includes, among other things, implantable medical device 110 and lead system 108. In various embodiments, implantable medical device 110 is an implantable CRM device including one or more of a pacemaker, a cardioverter/defibrillator, a cardiac resynchronization therapy (CRT) device, a cardiac remodeling control therapy (RCT) device, a neural stimulator, a drug delivery device or a drug delivery controller, and a biological therapy device. As illustrated in FIG. 1, implantable medical device 110 is implanted in a body 102. In various embodiments, lead system 108 includes leads for sensing physiological signals and delivering pacing pulses, cardioversion/defibrillation shocks, neural stimulation pulses, pharmaceutical agents, biological agents, and/or other types of energy or substance for treating cardiac disorders. In one embodiment, lead system 108 includes one or more pacing-sensing leads each including at least one electrode placed in or on a heart 101 for sensing electrogram and/or delivering pacing pulses. In other embodiments, electrodes placed in body 102 but away from heart 101 are used to sense physiological signals and deliver pacing pulses, cardioversion/defibrillation shocks, neural stimulation pulses, pharmaceutical agents, biological agents, and/or other types of energy or substance for treating cardiac disorders. In a specific embodiment, one or more electrodes are incorporated onto implantable medical device 110 for subcutaneous placement.

Implantable medical device 110 includes a cardiac pacing and post-ischemia therapy system 120. Pacing and post-ischemia therapy system 120 delivers a chronic pacing therapy, such bradycardia pacing therapy, CRT, and RCT, through lead system 108 while detecting an ischemic state indicative of occurrences of ischemic event. In one embodiment, pacing and post-ischemia therapy system 120 also delivers one of more of cardioversion/defibrillation therapy, neural stimulation therapy, drug therapy, and biological therapy as part of the chronic therapy. When the ischemia state indicates the occurrence of an ischemia event, pacing and post-ischemia therapy system 120 adjusts the chronic pacing therapy, if necessary, and initiates a post-ischemia therapy including, but not limited to, one or more of a post-ischemia pacing therapy, a post-ischemia neural stimulation therapy, a post-ischemia drug therapy, and a post-ischemia biological therapy. Pacing and post-ischemia therapy system 120 includes a feedback control system that senses one or more signals each indicative of the effectiveness of the chronic pacing therapy and/or the effectiveness of the post-ischemia therapy to initiate, suspend, terminate, adjust, and/or titrate each of these therapies.

External system 125 allows a user such as a physician or other caregiver to control the operation of implantable medical device 110 and obtain information acquired by implantable medical device 110. In one embodiment, external system 125 includes a programmer communicating with implantable medical device 110 bi-directionally via telemetry link 115. In another embodiment, external system 125 is a patient management system including an external device communicating with a remote device through a telecommunication network. The external device is within the vicinity of implantable medical device 110 and communicates with implantable medical device 110 bi-directionally via telemetry link 115. The remote device allows the user to monitor and treat a patient from a distant location. The patient monitoring system is further discussed below, with reference to FIG. 7.

Telemetry link 115 provides for data transmission from implantable medical device 110 to external system 125. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). Telemetry link 115 also provides for data transmission from external system 125 to implantable medical device 110. This includes, for example, programming implantable medical device 110 to acquire physiological data, programming implantable medical device 110 to perform at least one self-diagnostic test (such as for a device operational status), informing implantable medical device 110 of an external detection of the ischemia state, and programming implantable medical device 110 to deliver at least one therapy.

Figure 2:
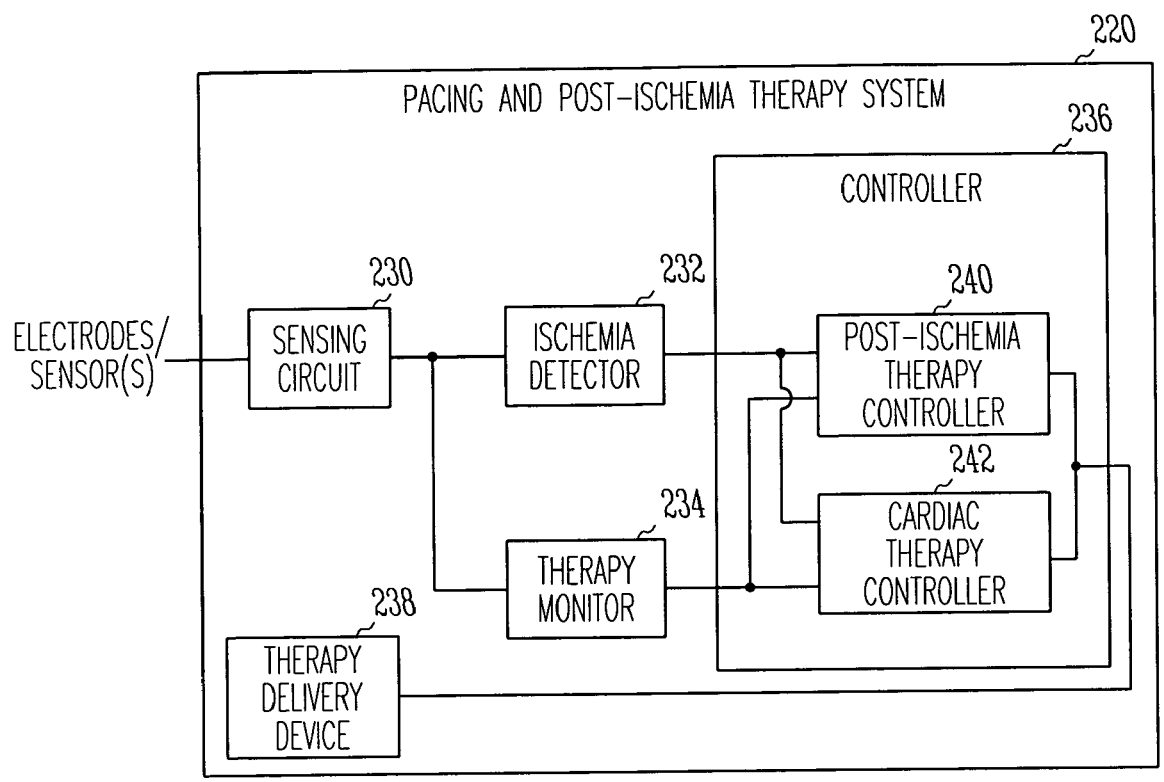
FIG. 2 is a block diagram illustrating an embodiment of a pacing and post-ischemia therapy system of an implantable medical device of the implantable system.

FIG. 2 is a block diagram illustrating an embodiment of a pacing and post-ischemia therapy system 220. Pacing and post-ischemia therapy system 220 is an embodiment of pacing and post-ischemia therapy system 120 and includes a sensing circuit 230, an ischemia detector 232, a therapy delivery device 238, a therapy monitor 234, and a controller 236.

Sensing circuit 230 senses one or more physiological signals including one or more ischemia-indicating signals and one or more therapy-monitoring signals. In one embodiment, at least one of the one or more physiological signals is both an ischemia-indicating signals and a therapy-monitoring signal. In various embodiments, the one or more therapy-monitoring signals indicate cardiac condition and/or hemodynamic performance, including effects of each therapy delivered by pacing and post-ischemia therapy system 220. Ischemia detector 232 detects the ischemic state from the one or more ischemia-indicating signals sensed by sensing circuit 230. The ischemic state indicates when an ischemic event is occurring. Therapy delivery device 238 delivers a post-ischemia therapy and a chronic therapy. Therapy monitor 234 produces one or more therapy-monitoring parameters from the one or more therapy-monitoring signals sensed by sensing circuit 230. The one or more therapy-monitoring parameters include one or more post-ischemia therapy-monitoring parameters and one or more chronic therapy-monitoring parameters. The one or more post-ischemia therapy-monitoring parameters each indicate effectiveness of the post-ischemia therapy. The one or more chronic therapy-monitoring parameters each indicate effectiveness of the chronic therapy. In one embodiment, at least one of the therapy-monitoring parameters is used as both a post-ischemia therapy-monitoring parameter and a chronic therapy-monitoring parameter. Controller 236 includes a post-ischemia therapy controller 240 and a chronic therapy controller 242. Post-ischemia therapy controller 240 initiates the delivery of the post-ischemia therapy and adjusts the delivery of the post-ischemia therapy based on the ischemic state detected by ischemic detector 232 and the one or more post-ischemia therapy-monitoring parameters produced by therapy monitor 234. Chronic therapy controller 242 adjusts the delivery of the chronic therapy base on the ischemic state detected by ischemic detector 232 and the one or more chronic therapy-monitoring parameters produced by therapy monitor 234. In one embodiment, the post-ischemia therapy and the chronic therapy are adjusted using the same therapy-monitoring parameter(s) produced by therapy monitor 234. In another embodiment, the post-ischemia therapy and the chronic therapy are adjusted using substantially different therapy-monitoring parameters produced by therapy monitor 234.

Figure 3:
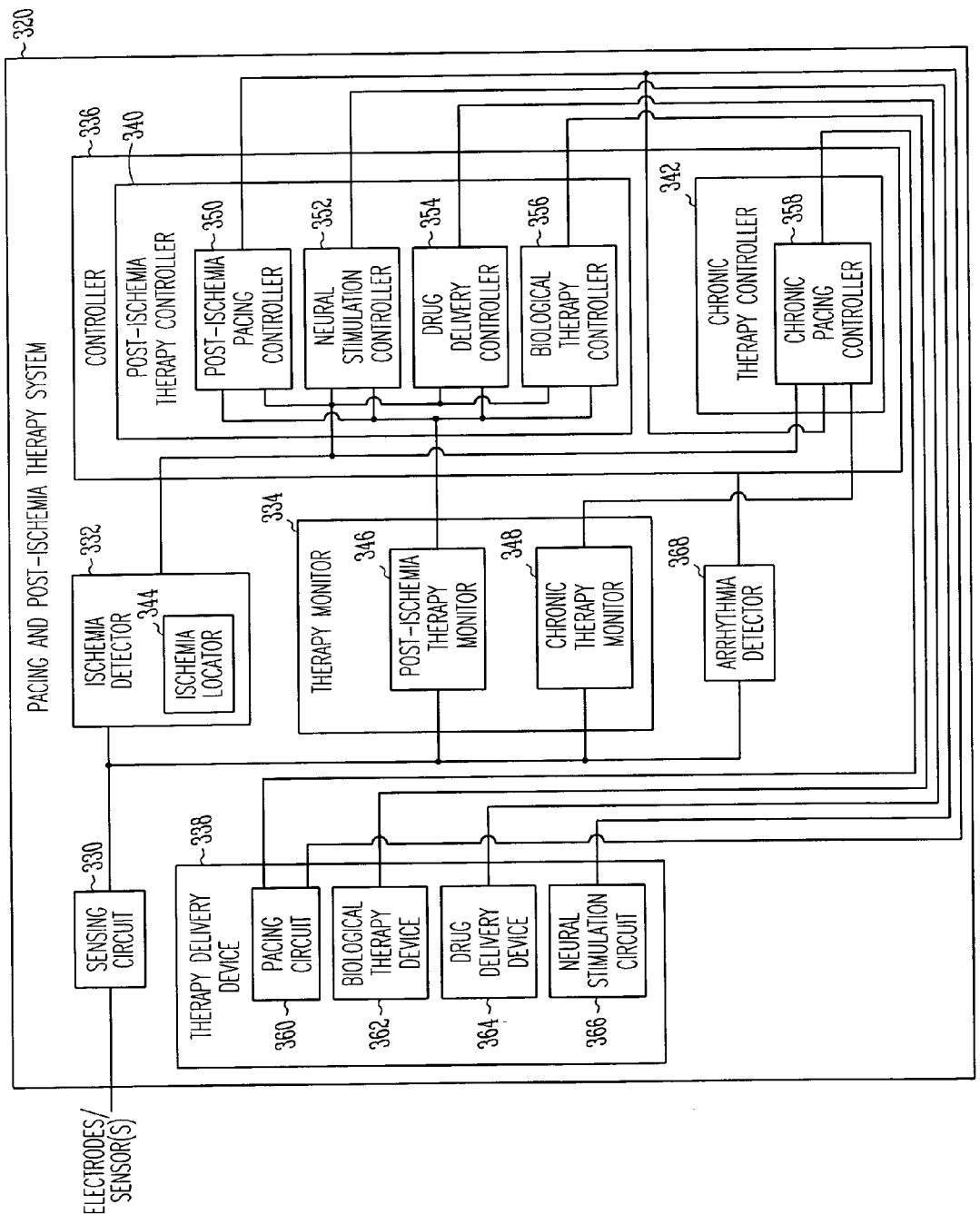
FIG. 3 is a block diagram illustrating a specific embodiment of the pacing and post-ischemia therapy system.

FIG. 3 is a block diagram illustrating an embodiment of a pacing and post-ischemia therapy system 320. Pacing and post-ischemia therapy system 320 is a specific embodiment of pacing and post-ischemia therapy system 220 and includes a sensing circuit 330, an ischemia detector 332, a therapy delivery device 338, a therapy monitor 334, an arrhythmia detector 368, and a controller 336.

Sensing circuit 330 senses the one or more physiological signals through one or more of implantable electrodes/sensors such as endocardial electrodes, epicardial electrodes, and subcutaneous electrodes, impedance sensor, pressure sensor, accelerometer, acoustic sensor such as microphone, strain sensor, and other sensors providing for the sensing of the one or more physiological signals. The one or more physiological signals sensed by sensing circuit 330 include the one or more ischemia-indicating signals used by ischemia detector 332 for detecting the ischemia state and the one or more therapy-monitoring signals used by therapy monitor 334 for producing one or more therapy-monitoring parameters. Examples of such physiological signals include cardiac signals such as electrogram and electrocardiogram (ECG), blood pressure signal, impedance signal, accelerometer signal indicative of heart sounds and/or activity level, acoustic signal indicative of heart sounds, and strain signal indicative of cardiac wall motion.

Ischemia detector 332 detects the ischemic state from the one or more ischemia-indicating signals. Ischemia detector 332 includes an ischemia analyzer running an automatic ischemia detection algorithm to detect the ischemic state from the one or more ischemia-indicating signals. In one embodiment, ischemia detector 332 produces an ischemia alert signal when the ischemic state indicates that an ischemic event, such as an acute MI, has occurred. In a specific embodiment, the ischemia signal is transmitted to external system 125 for producing an alarm signal and/or a warning message for the patient and/or a physician or other caregiver. In another specific embodiment, implantable medical device 110 produces an alarm signal and/or a warning message for the patient, such as by producing an audible tone or message.

In one embodiment, ischemia detector 332 detects the ischemic state from one or more cardiac signals. Sensing circuit 330 includes a cardiac sensing circuit. In a specific example, cardiac signals are sensed using a wearable vest or a pendant including embedded electrodes configured to sense surface biopotential signals indicative of cardiac activities. The sensed surface biopotential signals are transmitted to implantable medical device 110 via telemetry. In another specific embodiment, ischemia detector 332 detects the ischemic state from one or more wireless ECG signals. Sensing circuit 330 includes a wireless ECG sensing circuit. A wireless ECG is a signal approximating the surface ECG and is acquired without using surface (skin contact) electrodes. An example of a circuit for sensing the wireless ECG is discussed in U.S. patent application Ser. No. 10/795,126, entitled "WIRELESS ECG IN IMPLANTABLE DEVICES," filed on Mar. 5, 2004, assigned to Cardiac Pacemakers, Inc., which is incorporated herein by reference in its entirety. Examples of wireless ECG-based ischemia detection are is discussed in U.S. patent application Ser. No. 10/955,397, entitled "CARDIAC ACTIVATION SEQUENCE MONITORING AND TRACKING," filed on Mar. 14, 2005, and U.S. patent application Ser. No. 11/079,744, entitled "CARDIAC ACTIVATION SEQUENCE MONITORING FOR ISCHEMIA DETECTION," filed on Mar. 14, 2005, both assigned to Cardiac Pacemakers, Inc., which are incorporated herein by reference in their entirety. The sensing of wireless ECG is further discussed below, with reference to FIG. 4. In another embodiment, ischemia detector 332 detects the ischemic state from one or more electrogram signals. Sensing circuit 330 includes an electrogram sensing circuit. Examples of an electrogram-based ischemia detector are discussed in U.S. Pat. No. 6,108,577, entitled, "METHOD AND APPARATUS FOR DETECTING CHANGES IN ELECTROCARDIOGRAM SIGNALS," and U.S. patent application Ser. No. 09/962,852, entitled "EVOKED RESPONSE SENSING FOR ISCHEMIA DETECTION," filed on Sep. 25, 2001, both assigned to Cardiac Pacemakers, Inc., which are incorporated herein by reference in their entirety.

In another embodiment, ischemia detector 332 detects the ischemic state from one or more impedance signals. Sensing circuit 330 includes an impedance sensing circuit to sense one or more impedance signals each indicative of a cardiac impedance or a transthoracic impedance. Ischemia detector 332 includes an electrical impedance based sensor using a low carrier frequency to detect the ischemic state from an electrical impedance signal. Tissue electrical impedance has been shown to increase significantly during ischemia and decrease significantly after ischemia, as discussed in Dzwonczyk, et al. *IEEE Trans. Biomed. Eng.*, 51(12): 2206-09 (2004). The ischemia detector senses low frequency electrical impedance signal between electrodes interposed in the heart, and detects the ischemia as abrupt changes in impedance (such as abrupt increases in amplitude or phase angle). In one embodiment, ischemia detector 332 detects the ischemic state from local impedance signals that indicate regional mechanical delays due to slowed activation in an ischemic region.

In another embodiment, ischemia detector 332 detects the ischemic state from one or more signals indicative of heart sounds. Sensing circuit 330 includes a heart sound sensing circuit. The heart sound sensing circuit senses the one or more signals indicative of heart sounds using one or more sensors such as accelerometers and/or microphones. Such sensors are included in implantable medical device 110 or incorporated into lead system 108. Ischemia detector 332 detects the ischemic state by detecting predetermined type heart sounds, predetermined type heart sound components, predetermined type morphological characteristics of heart sounds, or other characteristics of heart sounds indicative of ischemia.

In another embodiment, ischemia detector 332 detects the ischemic state from one or more pressure signals. Sensing circuit 330 includes a pressure sensing circuit coupled to one or more pressure sensors. In a specific embodiment, the pressure sensor is an implantable pressure sensor sensing a signal indicative of an intracardiac or intravascular pressure whose characteristics are indicative of ischemia.

In another embodiment, ischemia detector 332 detects the ischemic state from one or more accelerometer signals each indicative of regional cardiac wall motion. Sensing circuit 330 includes a cardiac motion sensing circuit coupled to one or more accelerometers each incorporated into a portion of a lead positioned on or in the heart. Ischemia detector 332 detects ischemia as an abrupt decrease in the amplitude of local accelerometer signals or an increase in time delay between local accelerometer signals from different cardiac regions.

In another embodiment, ischemia detector 332 detects the ischemic state from a heart rate variability (HRV) signal indicative of HRV. Sensing circuit 330 includes an HRV sensing circuit to sense the HRV and produce the HRV signal, which is representative of an HRV parameter. HRV is the beat-to-beat variance in cardiac cycle length over a period of time. The HRV parameter includes any parameter being a measure of the HRV, including any qualitative expression of the beat-to-beat variance in cardiac cycle length over a period of time. In a specific embodiment, the HRV parameter includes the ratio of Low-Frequency (LF) HRV to High-Frequency (HF) HRV (LF/HF ratio). The LF HRV includes components of the HRV having frequencies between about 0.04 Hz and 0.15 Hz. The HF HRV includes components of the HRV having frequencies between about 0.15 Hz and 0.40 Hz. The ischemia detector detects ischemia when the LF/HF ratio exceeds a predetermined threshold. An example of an LF/HF ratio-based ischemia detector is discussed in U.S. patent application Ser. No. 10/669,168, entitled "METHOD FOR ISCHEMIA DETECTION BY IMPLANTABLE CARDIAC DEVICE," filed on Sep. 23, 2003, assigned to Cardiac Pacemakers, Inc., which is incorporated herein by reference in its entirety.

In another embodiment, ischemia detector 332 detects the ischemic state from a signal indicative of cardiac wall motion sensed by one or more strain sensors such as strain gauge sensors each incorporated into lead system 108 to sense a signal indicative of bending forces applied onto a lead. Sensing circuit 330 includes a strain signal sensing circuit coupled to the one or more strain sensors. The timing and amplitude of the bending force reflect the cardiac wall motion in the region where each strain sensor is placed, and such regional cardiac wall motion indicates whether the region is ischemic.

In another embodiment, ischemia detector 332 detects the ischemic state from a signal indicative changes in blood enzyme levels, such as levels of troponins and creatine-kinases (CK, CK-MB) in blood, as a result of myocardial stress or damage associated with ischemia. Sensing circuit 330 includes a blood enzyme level sensing circuit coupled to an implantable chemoreceptor that detects such changes in blood enzyme levels. Ischemia detector 332 detects ischemia as an abrupt change in a blood enzyme level.

In one embodiment, ischemia detector 332 includes an ischemia locator 344 to locate an ischemic region in heart 101. The ischemic region indicates the location or the approximate location of ischemic tissue, including infarct tissue, i.e., cardiac tissue whose characteristics are substantially affected by an ischemic event, including acute MI. In various embodiments, ischemia locator 344 uses a plurality of electrodes or sensors to locate the ischemic region by analyzing the signals sensed through these electrodes or sensors. Specific examples of locating the ischemic region using multiple electrodes are further discussed below, with reference to FIGS. 4 and 5.

Therapy delivery device 338 delivers one or more therapies. In one embodiment, therapy delivery device 338 delivers one or more therapies to heart 101 through lead system 108. In another embodiment, therapy delivery device 338 also delivers one or more therapies to other organs or regions of body 102. In one embodiment, as illustrated in FIG. 3, therapy delivering device 338 includes a pacing circuit 360, a biological therapy device 362, a drug delivery device 364, and a neural stimulation circuit 366. In various embodiments, therapy delivering device 338 includes any one or more of pacing circuit 360, biological therapy device 362, drug delivery device 364, and neural stimulation circuit 366, depending on the type of the post-ischemia and chronic therapies intended to be delivered by implantable medical device 110. In various embodiments, therapy delivering device 338 includes additional therapeutic modules such as a cardioversion/defibrillation circuit. The delivery of the one or more therapies is controlled by controller 336.

Therapy monitor 334 produces one or more therapy-monitoring parameters. Examples of such therapy-monitoring parameters include QRS width, ST-segment elevation, change in dominant orientation vector from wireless ECG, blood pressure, parameters derived from blood pressure (e.g., rate of pressure change and pulse pressure), regional impedance, amplitude of predetermined type heart sounds (e.g., S3 and S4), magnitude of regional cardiac wall motion, and any other parameters derived from signals sensed by sensing circuit 230 or 330. Each of such parameters indicates the effectiveness of at least one therapy delivered from therapy monitor 334. Therapy monitor 334 includes a post-ischemia therapy monitor 346 and a chronic therapy monitor 348. Post-ischemia therapy monitor 346 produces the one or more post-ischemia therapy-monitoring parameters from the one or more post-ischemia therapy-monitoring signals. The one or more post-ischemia therapy-monitoring parameters each indicate the effectiveness of the post-ischemia therapy. Chronic therapy monitor 348 produces the one or more chronic therapy-monitoring parameters from the one or more chronic therapy-monitoring signal of the at least one therapy-monitoring signal. The one or more chronic therapy-monitoring parameters each indicate the effectiveness of the chronic therapy.

Controller 336 controls the delivery of the one or more therapies based on the ischemic state, the ischemic region, and the one or more therapy-monitoring parameters. Controller 336 includes a post-ischemia therapy controller 340 and a chronic therapy controller 342. Post-ischemia therapy controller 340 initiates the delivery of the post-ischemia therapy and adjusts the delivery of the post-ischemia therapy based on the detected ischemic state and the one or more post-ischemia therapy-monitoring parameters. Chronic therapy controller 342 adjusts the delivery of the chronic therapy based on the detected ischemic state and the one or more chronic therapy-monitoring parameters. In one embodiment, post-ischemia therapy controller 340 stops the delivery of the post-ischemia therapy when, for example, the detected ischemic state indicates that the ischemic event is no longer occurring and/or the one or more post-ischemia therapy-monitoring parameters no longer indicate a need for the post-ischemia therapy. In one embodiment, the post-ischemia therapy and the chronic therapy are substantially different type therapies. In one embodiment, the post-ischemia therapy and the chronic therapy are the same type therapy but use substantially different parameter(s), and post-ischemia therapy controller 340 initiates the delivery of the post-ischemia therapy by adjusting one or more parameters of the chronic therapy.

In one embodiment, as illustrated in FIG. 3, post-ischemia therapy controller 340 includes a post-ischemia pacing controller 350, a neural stimulation controller 352, a drug delivery controller 354, and a biological therapy controller 356. In various embodiments, post-ischemia therapy controller 340 includes any one or more of post-ischemia pacing controller 350, neural stimulation controller 352, drug delivery controller 354, and biological therapy controller 356, depending on the available components of therapy delivery device 338. Chronic therapy controller 342 includes a chronic pacing controller 358. In other embodiments, post-ischemia therapy controller 340 and chronic therapy controller 342 each includes additional specific therapeutic controllers to control the delivery of additional types of suitable therapy. Post-ischemia pacing controller 350 initiates a post-ischemia pacing therapy and controls the delivery of pacing pulses from pacing circuit 360 to the ischemic region. In one embodiment, chronic pacing controller 358 controls the delivery of pacing pulses to a plurality of locations in heart 101 from pacing circuit 360. When the detected ischemic state indicates the occurrence of an ischemic event, chronic pacing controller 358 adjusts one or more global pacing parameters to reduce the overall workload on heart 101, and post-ischemia pacing controller 350 adjusts one or more regional pacing parameters to provide pre-excitation of the ischemic region to reduce the stress and work load of the ischemic region. For example, when the chronic therapy is CRT pacing in an atrial tracking mode, chronic pacing controller 358 reduces the lower rate limit, and post-ischemia pacing controller 350 shortens an atrioventricular (AV) delay at the located ischemic region (i.e., the AV delay associated with the electrode closest to the ischemic region). An example of post-ischemia pacing is discussed in U.S. patent application Ser. No. 10/005,184, entitled "METHOD AND APPARATUS FOR MINIMIZING POST-INFARCT VENTRICULAR REMODELING," filed Dec. 5, 2001, assigned to Cardiac Pacemakers, Inc., which is incorporated herein by reference in its entirety. In another embodiment, when the detected ischemic state indicates the occurrence of an ischemic event, post-ischemia pacing controller 350 initiates one or more cardiac protection pacing sequences. In a specific embodiment, chronic pacing controller 358 suspends the delivery of the chronic therapy during the one or more cardiac protection pacing sequences. Examples of post-ischemia cardiac protection pacing sequences are discussed in U.S. patent application Ser. No. 11/129,058, entitled "METHOD AND APPARATUS FOR DELIVERING PACING PULSES USING A CORONARY STENT," filed on May 13, 2005 and U.S. patent application Ser. No. 11/129,050, entitled "METHOD AND APPARATUS FOR CARDIAC PROTECTION PACING," filed on May 13, 2005, both assigned to Cardiac Pacemakers, Inc., which are incorporated herein by reference in their entirety.

Neural stimulation controller 352 initiates a post-ischemia neural stimulation therapy and controls the delivery of neural stimulation pulses from neural stimulation circuit 366. Examples of post-ischemia neural stimulation therapy are discussed in U.S. patent application Ser. No. 10/745,920, entitled "BAROREFLEX STIMULATION TO TREAT ACUTE MYOCARDIAL INFARCTION," filed Dec. 24, 2003, and U.S. patent application Ser. No. 11/075,838, entitled "IMPLANTABLE VAGAL STIMULATOR FOR TREATING CARDIAC ISCHEMIA," filed May 9, 2005, both assigned to Cardiac Pacemakers, Inc., which are incorporated herein by reference in their entirety.

Drug delivery controller 354 initiates a post-ischemia drug therapy and controls the delivery of one or more pharmaceutical agents from drug delivery device 364. Examples of post-ischemia drug therapy is discussed in U.S. patent application Ser. No. 10/645,823, entitled "METHOD AND APPARATUS FOR MODULATING CELLULAR METABOLISM DURING POST-ISCHEMIA OR HEART FAILURE," filed Aug. 21, 2003, assigned to Cardiac Pacemakers, Inc., which is incorporated herein by reference in its entirety. In one embodiment, drug delivery controller 354 initiates the post-ischemia drug therapy to deliver a thrombolytic agent.

Biological therapy controller 356 initiates a post-ischemia biological therapy and controls the delivery of one or more biological substances and/or one or more signals that control a biological therapy from biological therapy device 362. Examples of the post-ischemia biological therapy are discussed in U.S. patent application Ser. No. 10/862,716, entitled "METHOD AND APPARATUS TO MODULATE CELLULAR REGENERATION POST MYOCARDIAL INFARCT," filed Jun. 7, 2004, assigned to Cardiac Pacemakers, Inc., which is incorporated herein by reference in its entirety. In one embodiment, the post-ischemia biological therapy includes a stem cell therapy. In a specific embodiment, biological therapy controller 356 controls the delivery of one or more agents from biological therapy device 362 and/or drug delivery device 364 and the delivery of pacing pulses from pacing circuit 360. The one or more agents are delivered in an amount effective to enhance stem cell migration, implantation and/or proliferation in the ischemic region. The pacing pulses are delivered to heart 101 to reduce cardiac wall stress or workload in the ischemic region to provide for a favorable environment for the stem cell migration, implantation and/or proliferation.

Arrhythmia detector 368 detects predetermined type arrhythmias including bradyarrhythmias and tachyarrhythmias from one or more cardiac signals sensed by sensing circuit 330. In response to the detection of a predetermined type arrhythmia, controller 336 initiates an anti-arrhythmia therapy. In one embodiment, controller 336 suspends the post-ischemia therapy and/or the chronic therapy, when necessary, to deliver the anti-arrhythmia therapy. For example, in response to a detected tachyarrhythmia caused by the ischemic event, controller 336 pauses the post-ischemia therapy and/or the chronic therapy to deliver a cardioversion/defibrillation shock pulse and resumes the post-ischemia therapy and/or the chronic therapy when the tachyarrhythmia is terminated.

Figure 4:
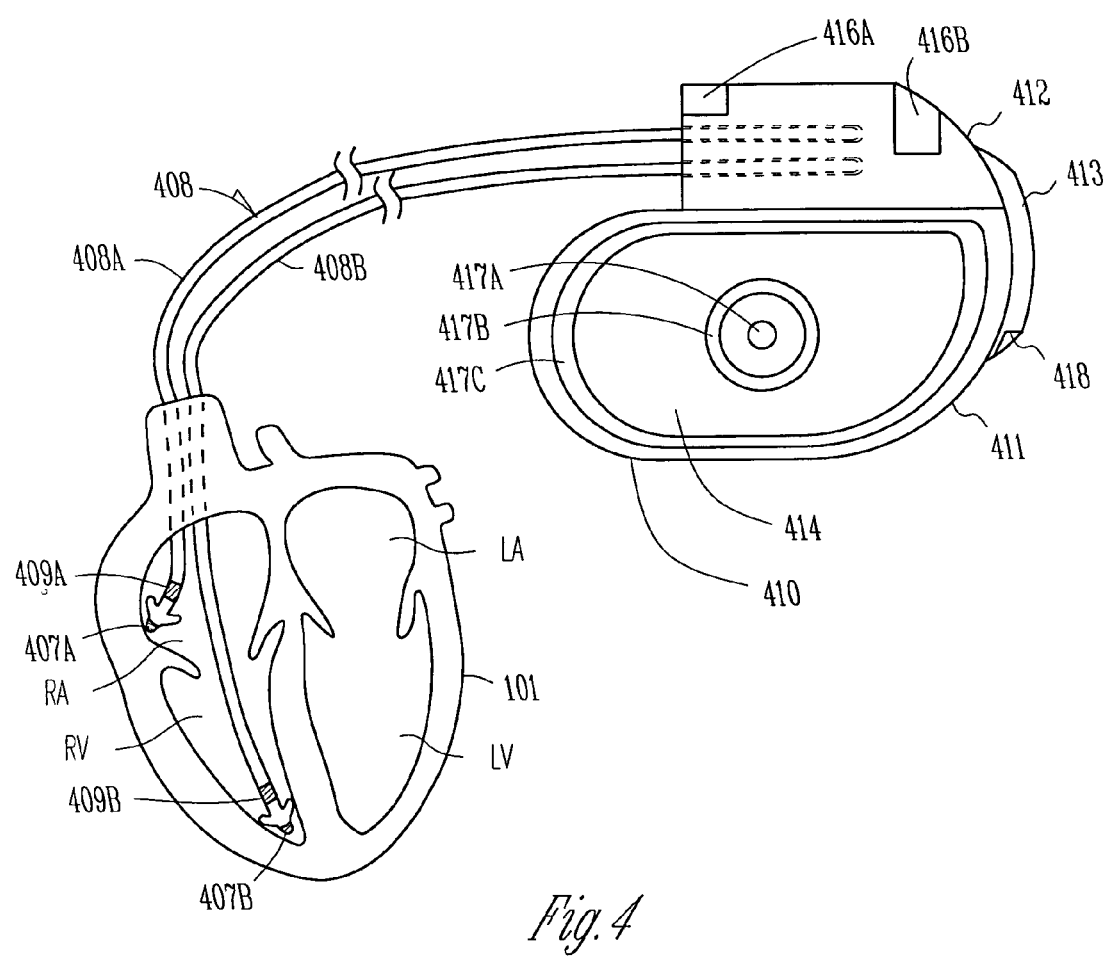
FIG. 4 is an illustration of an embodiment of an electrode system for detecting an ischemic state and/or locating an ischemic region in a heart.

FIG. 4 is an illustration of an embodiment of an electrode system for detecting the ischemic state and/or locating the ischemic region using the wireless ECG. Each wireless ECG signal is sensed using a pair of implantable electrodes. These implantable electrodes are selected from the electrodes including, but not being limited to, those illustrated in FIG. 4. In one embodiment, the electrodes are selected to allow for sensing electrical activities from a substantial portion of the heart, up to the entire heart.

In one embodiment, one or more pacing electrodes of a lead system 408 are used as one or more electrodes for the wireless ECG sensing. Lead system 408 is an embodiment of lead system 108. In one embodiment, as illustrated in FIG. 4, lead system 408 includes an atrial lead 408A and a ventricular lead 408B. The one or more electrodes are selected from, for example, a tip electrode 407A of atrial lead 408A, a ring electrode 409A atrial lead 408A, a tip electrode 407B of ventricular lead 408B, and a ring electrode 409B of ventricular lead 408B. Leads 408A-B each have a proximal end connected to an implantable medical device 410 and a distal end for intracardiac or epicardial placement. Each tip electrode is located in the distal end of a lead. Each ring electrode is located near the distal end, at a predetermined distance from the tip electrode. In one specific embodiment, atrial lead 408A is an RA lead, and ventricular lead 408B is an RV lead. In another specific embodiment, atrial lead 408A is an RA lead, and ventricular lead 408B is an LV lead. In another specific embodiment, lead system 408 includes only one or more atrial leads. In another specific embodiment, lead system 408 includes only one or more ventricular leads. In other specific embodiments, lead system 408 includes more than one atrial lead or more than one ventricular lead.

Implantable medical device 410 is an embodiment of implantable medical device 110 and includes a hermetically sealed can 411 to house its circuit. Can 411 has an outer surface subject to contact with body tissue. Can 411 includes or provides for a base of a can electrode 414 that is selectable as one of the electrodes for the wireless ECG sensing. At least a portion of the outer surface of can 411 is made of electrically conductive material. In one embodiment, can 411 is used as can electrode 414. In one specific embodiment, can electrode 414 includes at least one conductive portion of can 411. In another embodiment, can electrode 414 is incorporated onto the outer surface of can 411. Can electrode 414 is electrically insulated from any conductive portion of can 411 using a non-conductive layer. In one specific embodiment, a hermetically sealed feedthrough including a conductor provides for an electrical connection between can electrode 414 and the circuit housed in can 411.

A header 412 is attached to can 411 and includes connectors providing for electrical access to the circuit housed in can 411. In one embodiment, one or more header electrodes 416A-B are incorporated into the header. Header electrodes 416A-B are each selectable as one of the electrodes for the wireless ECG sensing.

In one embodiment, two or more concentric electrodes 417A-C are incorporated onto the outer surface of can 411. Each of the concentric electrodes 417A-C is selectable as one of the electrodes for the wireless ECG sensing. Concentric electrodes 417A-C are insulated from the conductive portion of can 411 with a non-conductive layer and connected to the circuit housed in can 411 via hermetically sealed feedthroughs. In one embodiment, two electrodes, including an inner electrode and an outer electrode, are selected from concentric electrodes 417A-C for the wireless ECG sensing. In one embodiment, the outer electrode has a ring shape. In another embodiment, the outer electrode has a shape approaching the contour of can 411.

In one embodiment, implantable medical device 410 includes an antenna 413 for the far-field RF telemetry. Antenna 413 is electrically connected to the circuit housed in can 411. In one embodiment, antenna 413 projects from header 412 and extends along one side of can 411. In one embodiment, antenna 413 includes a metal conductor with a distal portion exposed for functioning as an antenna electrode 418, which is selectable as one of the electrodes for the wireless ECG sensing.

The electrodes illustrated in FIG. 4 are intended to be examples but not limitations. Other electrode configurations are usable as long as they provide for sensing of signals that approximates the surface ECG or otherwise contains valuable information for diagnostic and/or therapeutic purposes. In one embodiment, the electrodes for the wireless ECG sensing are selected from the electrodes in one or more leads of lead system 108 (e.g., electrodes 407A, 409A, 407B, and 409B). In this embodiment, the wireless ECG sensing differs from the electrogram sensing in that their corresponding morphologies reflect the differences in the source of the wireless ECG and the intracardiac electrogram. The electrodes for the wireless ECG sensing are selected to allow for sensing electrical activities from a substantial portion of the heart. This generally means that each pair of electrodes for sensing one wireless ECG includes only one electrode from each lead of lead system 408. In a specific embodiment, electrodes 409A and 409B are selected for the wireless ECG sensing. In another embodiment, the electrodes for the wireless ECG sensing are implantable subcutaneous electrodes. Examples of such implantable subcutaneous electrodes include, but are not limited to electrodes incorporated onto implantable medical device 410, such as can electrode 414, header electrodes 416A-B, concentric electrodes 417A-C, and antenna electrode 418. In this embodiment, the wireless ECG is referred to as subcutaneous ECG, which results from electrical activities of a substantial portion of the heart, up to the entire heart. In another embodiment, the electrodes for the wireless ECG sensing are selected from the electrodes in one or more leads of lead system 408 and the electrodes incorporated onto implantable medical device 410.

Examples of wireless ECG-based ischemia detection are discussed in U.S. patent application Ser. No. 10/955,397 and U.S. patent application Ser. No. 11/079,744. In one embodiment, multiple ECG vectors are sensed to allow ischemia locator 344 to locate the ischemic region by performing a vectorcardiographic analysis. In various embodiments in which multiple wireless ECG vectors are needed, multiple pairs of electrodes are selected, simultaneously or one at a time, for a multi-channel (multi-vector) wireless ECG sensing. The selection of electrode pairs for sensing the ECG vectors is determined by the need of ischemia detector 332 in detecting the ischemic state and the need of ischemia detector 344 in locating the ischemic region. In one embodiment, an ECG vector that provides for a reliable sensing for the purpose of detecting the ischemic state is selected. When two or more ECG vectors provide for the reliable sensing, the ECG vector showing the highest signal-to-noise ratio (SNR) for that purpose is selected. In one embodiment, an optimal linear combination of ECG vectors is formed to provide the highest SNR, such as discussed in U.S. patent application Ser. No. 10/741,814, entitled "SEPARATION OF A SUBCUTANEOUS CARDIAC SIGNAL FROM A PLURALITY OF COMPOSITE SIGNALS," filed on Dec. 19, 2003, assigned to Cardiac Pacemakers, Inc., which is incorporated herein by reference in its entirety.

Figure 5:
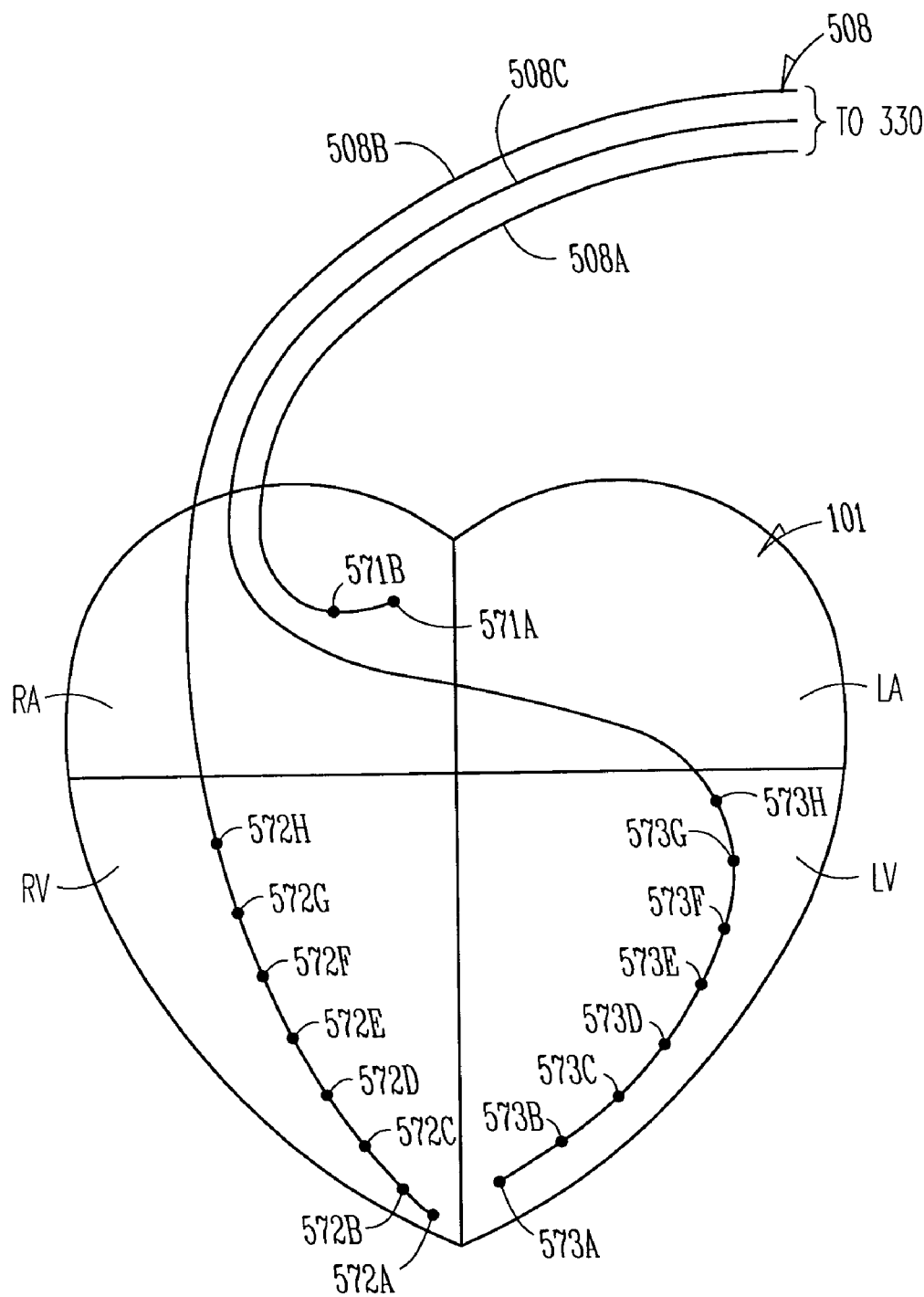
FIG. 5 is an illustration of an embodiment of another electrode system for detecting the ischemic state and/or locating the ischemic region in the heart.

FIG. 5 is an illustration of an embodiment of an electrode system for detecting the ischemic state and/or locating the ischemic region using electrograms and/or impedance signals. The electrode system includes a lead system 508 that allows for sensing of regional electrograms and/or regional impedances in and/or on heart 101.

Lead system 508 is an embodiment of lead system 108 and is connected to sensing circuit 330 for sensing electrograms and/or impedance signals. In one embodiment, as illustrated in FIG. 5, lead system 508 includes an atrial lead 508A, an RV lead 508B, and a LV lead 508C. Atrial lead 508A is an endocardial lead that includes endocardial electrodes 571A-B for placement in the RA. RV lead 508B is an endocardial or epicardial lead that includes endocardial or epicardial electrodes 572A-H for placement in or on the RV. LV lead 508C is an endocardial or epicardial lead that includes endocardial or epicardial electrodes 573A-H for placement in or on the LV.

In one embodiment, ischemia detector 332 detects the ischemia state from each of a plurality of electrograms sensed using at least one electrode selected from electrodes 572A-H and 573A-H. When the ischemic state indicates the occurrence of an ischemic event, ischemia locator 344 locates the ischemic region by identifying at least one electrode associated with an electrogram from which the occurrence of the ischemic event is detected.

In another embodiment, a plurality of electrodes selected from electrodes 572A-H and 573A-H are used to measure impedances. Ischemia detector 332 detects the ischemia state from each measured impedance. When the ischemic state indicates the occurrence of an ischemic event, such as by an abrupt change in the measured impedance, ischemia locator 344 locates the ischemic region by identifying at least one electrode associated with the measured impedance from which the occurrence of the ischemic event is detected.

In a further embodiment, one or more strain sensors are incorporated into each of leads 508B and 508C to sense signals indicative of regional cardiac wall motion. Ischemia detector 332 detects the ischemia state from the each of the signals indicative of region cardiac wall motion. When the ischemic state indicates the occurrence of an ischemic event, such as by an abrupt change in the regional cardiac wall motion, ischemia locator 344 locates the ischemic region by identifying at least one strain sensor associated with the signal from which the occurrence of the ischemic event is detected.

In one embodiment, ischemia locator 344 locates the ischemic region by using a combination of methods discussed in this document. In a specific embodiment, ischemia locator 344 first identifies an approximate ischemic region by analyzing wireless ECG vectors. Then, ischemia locator 344 further locates the ischemic region by analyzing electrograms and impedances sensed from the identified approximate ischemic region. The ischemic region is located by combining the results of localization of all the methods performed, such as by using fuzzy logic.

Figure 6:
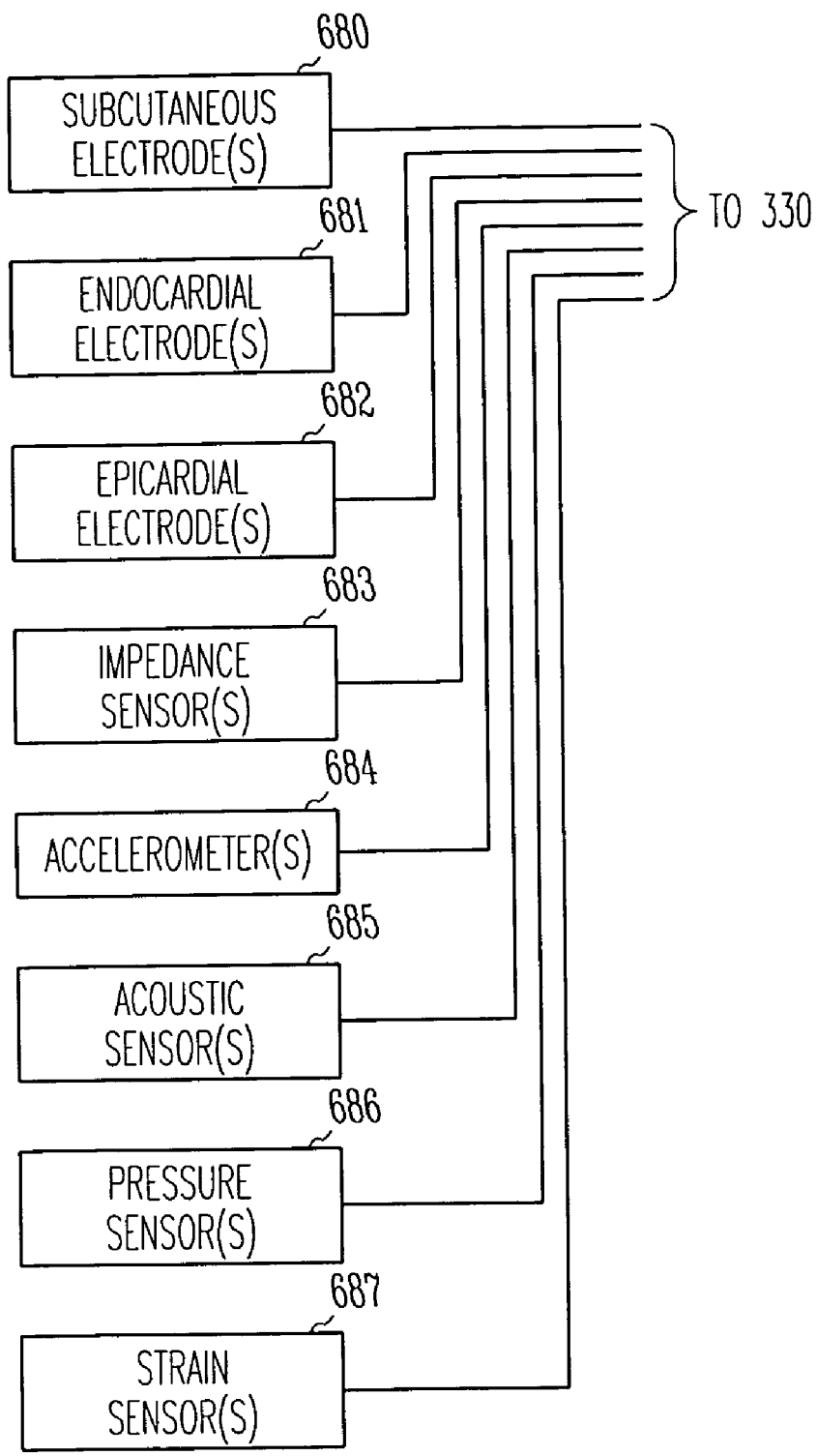
FIG. 6 is an illustration of an embodiment of an electrode/sensor system for detecting the ischemic state and/or locating the ischemic region in the heart.

FIG. 6 is an illustration of an embodiment of an electrode/sensor system for detecting the ischemic event and/or locating the ischemic region. In various embodiments, one or more of subcutaneous electrode(s) 680, endocardial electrodes(s) 681, epicardial electrodes 682, impedance sensor(s) 683, accelerometer(s) 684, acoustic sensor(s) 685, pressure sensor(s) 686, and strain sensor(s) 687 are coupled to sensing circuit 330 to allow sensing of the one or more physiological signals for detecting the ischemic state and monitoring the therapies as discussed in this document. In one embodiment, such electrodes and sensors are each electrically connected to implantable medical device 110. In another embodiment, one or more of such electrodes and sensors are electrically connected to another device that communicates with implantable medical device 110 via telemetry.

Figure 7:
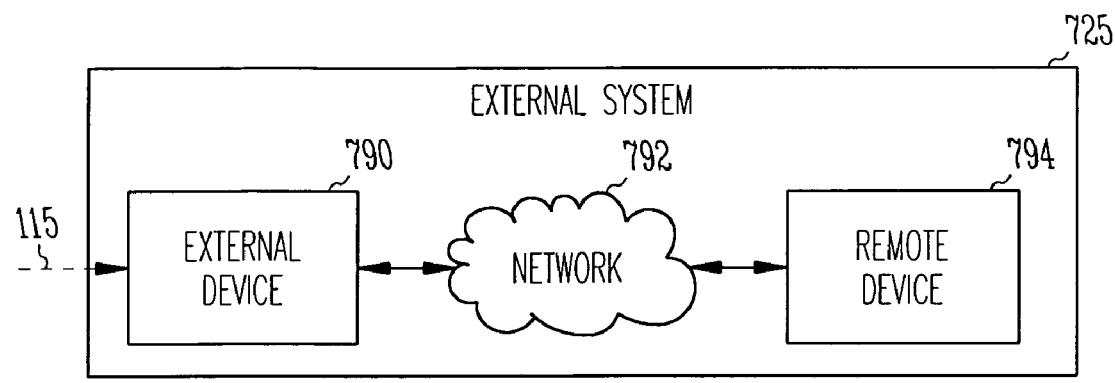
FIG. 7 is an illustration of an embodiment of the external system.

FIG. 7 is an illustration of an embodiment of an external system 725, which is a specific embodiment of external system 125. As illustrated in FIG. 7, external system 725 is a patient management system including an external device 790, a telecommunication network 792, and a remote device 794. External device 790 is placed within the vicinity of an implantable medical device and communicates with the implantable medical device via telemetry link 115. Remote device 794 is in one or more remote locations and communicates with external device 790 through network 792, thus allowing a physician or other caregiver to monitor and treat a patient from a distant location and/or allowing access to various treatment resources from the one or more remote locations. In one embodiment, remote device 794 receives the alarm signal and/or warning message associated with the ischemia alert signal produced by ischemia detector 332 and allows the physician or other caregiver to initiate and/or adjust a therapy from a location remote from the patient.

Figure 8:
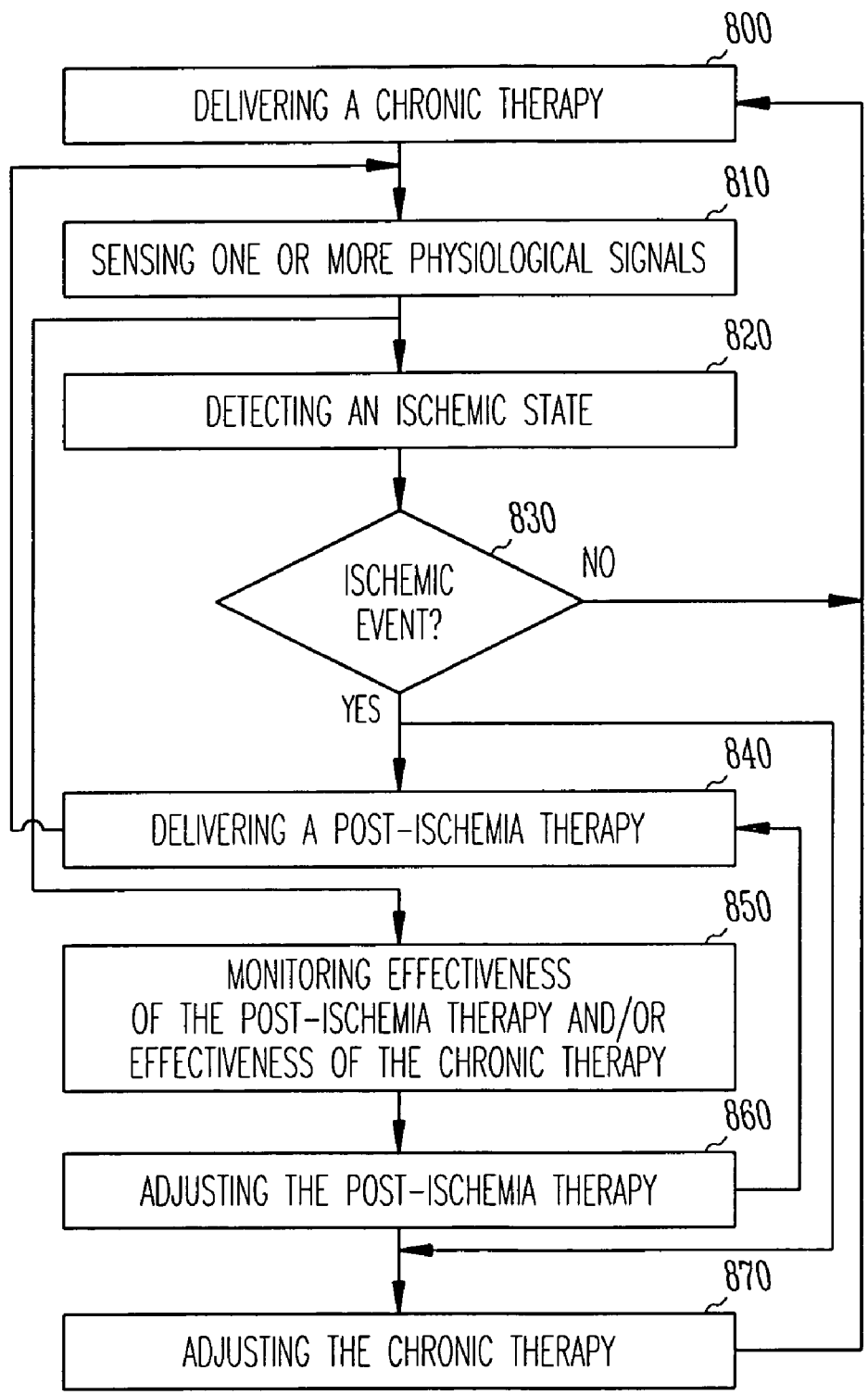
FIG. 8 is a flow chart illustrating an embodiment of a method for delivering chronic and post-ischemia therapies for treating a heart.

FIG. 8 is a flow chart illustrating an embodiment of a method for delivering chronic and post-ischemia therapies for treating a heart. In one embodiment, the method is performed by system 100.

A chronic therapy is delivered to treat a chronic cardiac condition of a patient at 800. The patient is diagnosed of a cardiac condition associated with the risk of occurrence of an ischemic event, such as an acute MI. In one embodiment, the chronic therapy is a chronic pacing therapy. Examples of the chronic pacing therapy include bradycardia pacing therapy, CRT, and RCT. In one example, the patient is a heart failure patient. In another example, the patient has suffered an MI and developed heart failure. While delivering a CRT therapy, the patient is monitored for recurring MI.

One or more physiological signals are sensed at 810. The one or more signals include one or more ischemia-indicating signals that allow for detection of an ischemic state of the patient and one or more therapy-monitoring signals allows for monitoring of therapies delivered to the patient. Examples of the one or more physiological signals include electrogram, wireless ECG signal, blood pressure signal, impedance signal, accelerometer signal indicative of heart sounds and/or activity level, acoustic signal indicative of heart sounds, and strain signal indicative of cardiac wall motion. In one embodiment, at least one physiological signal is used as both an ischemia-indicating signal and a therapy-monitoring signal. In one embodiment, the one or more ischemia-indicating signals and the one or more therapy-monitoring signals include substantially different signals.

The ischemic state is detected at 820 from the one or more ischemia-indicating signals. The ischemic state indicates the occurrence of each ischemic event. In one embodiment, an ischemic region is located by analyzing the one or more ischemia-indicating signals. The ischemic region includes ischemic or infarct cardiac tissue or is in the proximity of the ischemic or infarct cardiac tissue.

If the ischemia state indicates the occurrence of an ischemic event at 830, a post-ischemia therapy is delivered at 840. Examples of the post-ischemia therapy include a post-ischemia pacing therapy, a post-ischemia neural stimulation, a post-ischemia drug therapy, and a post-ischemia biological therapy. In one embodiment, the post-ischemia pacing therapy is delivered by adjusting one or more parameters of the chronic pacing therapy. The one or more physiological signals sensed at 810 include one or more post-ischemia therapy-monitoring signals allowing for monitoring of the post-ischemia therapy and one or more chronic therapy-monitoring signals allowing for monitoring of the chronic therapy. In one embodiment, at least one signal is used as both a post-ischemia therapy-monitoring signal and a chronic therapy-monitoring signal. In one embodiment, the one or more post-ischemia therapy-monitoring signals and the one or more chronic therapy-monitoring signals include substantially different signals.

The effectiveness of the post-ischemia therapy and/or the effectiveness of the chronic therapy are monitored at 850. One or more therapy-monitoring parameters are produced from the one or more therapy-monitoring signals. Examples of the one or more therapy-monitoring parameters include QRS width, ST-segment deviation, change in dominant orientation vector from wireless ECG, HRV parameter, blood pressure, parameters derived from blood pressure (e.g., rate of pressure change and pulse pressure), regional impedance, amplitude of predetermined type heart sounds (e.g., S3 and S4), magnitude of regional cardiac wall motion, and any other parameters derived from signals sensed by sensing circuit 230 or 330. In one embodiment, at least one post-ischemia therapy-monitoring parameter is produced from a post-ischemia therapy-monitoring signal, and at least one chronic therapy-monitoring parameter is produced from a chronic therapy-monitoring signal. The post-ischemia therapy-monitoring parameter indicates the effectiveness of the post-ischemia therapy. The chronic therapy-monitoring parameter indicates the effectiveness of the chronic therapy.

The post-ischemia therapy is adjusted according to the ischemic state and the one or more therapy-monitoring parameters at 860. After being initiated in response to the occurrence of the ischemic event, the post-ischemia therapy is adjusted based on the one or more therapy-monitoring parameters. In one embodiment, the post-ischemia therapy is delivered to the located ischemic region. In one embodiment, the delivery of the post-ischemia therapy is stopped when the ischemic state indicate that the ischemic event is no longer occurring and/or when the post-ischemia therapy-monitoring parameter indicates that the post-ischemia therapy is no longer needed.

The chronic therapy is adjusted according to the ischemic state and the one or more therapy-monitoring parameters at 870. In one embodiment, the chronic therapy is adjusted, to reduce the overall cardiac workload for example, when the ischemic state indicates the occurrence of the ischemic event. In one embodiment, the delivery of the chronic therapy is further adjusted, to restore its pre-ischemia parameters for example, when the ischemic state indicate that the ischemic event is no longer occurring and/or when the post-ischemia therapy-monitoring parameter indicates that the post-ischemia therapy is no longer needed. In one embodiment, the chronic therapy is adjusted using the chronic therapy-monitoring parameter regardless of whether the post-ischemia therapy is being delivered.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for treating a heart with an ischemic region, the system comprising:

a sensing circuit to sense one or more physiological signals including one or more ischemia-indicating signals and one or more therapy-monitoring signals;

an ischemia detector, coupled to the sensing circuit, to detect an ischemic state indicative of an occurrence of an ischemic event from the one or more ischemia-indicating signals, the ischemic detector including an ischemia locator adapted to locate the ischemic region;

a therapy delivery device including a pacing output circuit to deliver a post-ischemia therapy and a chronic pacing therapy each including delivering of pacing pulses;

a therapy monitor, coupled to the sensing circuit, to produce one or more therapy-monitoring parameters from the one or more therapy-monitoring signals, the one or more therapy-monitoring parameters each indicative of effectiveness of at least one of the post-ischemia therapy and the chronic pacing therapy; and a controller coupled to the ischemia detector, the therapy delivery device, and the therapy monitor, the controller including:

a post-ischemia therapy controller adapted to initiate a delivery of the post-ischemia therapy in response to the occurrence of the ischemic event as indicated by the detected ischemic state and to adjust the delivery of the post-ischemia therapy based on the detected ischemic state, the location of the ischemic region, and at least one post-ischemia therapy-monitoring parameter of the one or more therapy-monitoring parameters, the post-ischemic therapy controller including a post-ischemic pacing controller programmed to adjust one or more regional pacing parameters to provide pre-excitation of the ischemic region to reduce stress and workload of the ischemic region in response to the occurrence of the ischemic event; and a chronic therapy controller adapted to adjust a delivery of the chronic pacing therapy based on the detected ischemic state and at least one chronic therapy-monitoring parameter of the one or more therapy-monitoring parameters, the chronic therapy controller including a chronic pacing controller programmed to adjust one or more global pacing parameters to reduce overall workload on the heart in response to the occurrence of the ischemic event.

2. The system of claim 1, further comprising an implantable housing configured to house the sensing circuit, the ischemia detector, the therapy delivery device, the therapy monitor, and the controller.

3. The system of claim 2, wherein the post-ischemia therapy controller is adapted to cause the post-ischemia therapy to be delivered to the located ischemic region.

4. The system of claim 3, further comprising a plurality of implantable leads coupled to the sensing circuit, the implantable leads each including a plurality of electrodes to sense a plurality of regional electrograms, and wherein the ischemia locator is adapted to locate the ischemic region using the plurality of regional electrograms.

5. The system of claim 3, further comprising a plurality of implantable leads coupled to the sensing circuit, the implantable leads each including a plurality of electrodes to sense a plurality of regional impedance signals, and wherein the ischemia locator is adapted to locate the ischemic region using the plurality of regional impedance signals.

6. The system of claim 3, further comprising a plurality of implantable leads and a plurality of strain sensors incorporated into the implantable leads, and wherein the ischemia locator is adapted to locate the ischemic region using signals sensed by the plurality of strain sensors.

7. The system of claim 3, further comprising a plurality of electrodes incorporated onto the implantable housing to sense a plurality of subcutaneous electrocardiogram (ECG) vectors, and wherein the ischemia locator is adapted to locate the ischemic region by analyzing the plurality of subcutaneous ECG vectors.

8. The system of claim 1, wherein the post-ischemia therapy controller is adapted to initiate the delivery of the post-ischemia therapy by adjusting one or more parameters of the chronic pacing therapy.

9. The system of claim 1, wherein the chronic pacing controller is adapted to control the delivery of the chronic pacing therapy by adjusting one or more pacing parameters of the chronic pacing therapy based on the detected ischemic state and the at least one chronic therapy-monitoring parameter.

10. The system of claim 9, wherein the therapy delivery device further comprises a neural stimulation circuit adapted to deliver a post-ischemia neural stimulation therapy, and the post-ischemia therapy controller comprises a neural stimulation controller adapted to initiate and control the post-ischemia neural stimulation therapy.

11. The system of claim 9, wherein the therapy delivery device further comprises a drug delivery device adapted to deliver a post-ischemia drug therapy, and the post-ischemia therapy controller comprises a drug delivery controller adapted to initiate and control the post-ischemia drug therapy.

12. The system of claim 9, wherein the therapy delivery device further comprises a biological therapy device adapted to deliver a post-ischemia biological therapy including delivery of one or more biological substances, and the post-ischemia therapy controller comprises a biological therapy controller adapted to initiate and control the post-ischemia biological therapy.

13. The system of claim 9, wherein the post-ischemia pacing controller is adapted to control the delivery of the post-ischemia pacing therapy by adjusting one or more pacing parameters of the chronic pacing therapy for a pre-excitation of the ischemic region.

14. The system of claim 1, wherein the chronic pacing controller is programmed to lower a lower rate limit of the one or more global pacing parameters in response to the occurrence of the ischemic event, and the post-ischemia pacing controller is programmed to shorten at least an atrioventricular delay of the one or more regional pacing parameters, the atrioventricular delay associated with the ischemic region.

15. A method for treating a heart with an ischemic region, the method comprising:
    delivering a chronic pacing therapy;
    sensing one or more physiological signals;
    detecting an ischemic state indicative of an occurrence of an ischemic event from one or more ischemia-indicating signals of the one or more physiological signals;
    locating the ischemic region;
    initiating a delivery of a post-ischemia therapy including a post-ischemia pacing therapy during which pacing pulses are delivered to the ischemic region in response to the occurrence of the ischemic event as indicated by the detected ischemic state;
    producing one or more therapy-monitoring parameters from one or more therapy-monitoring signals of the one or more physiological signals, the one or more therapy-monitoring parameters each indicative of effectiveness of at least one of the chronic pacing therapy and the post-ischemia therapy; and
    adjusting the delivery of the chronic pacing therapy and the delivery of the post-ischemia therapy based on the detected ischemic state, the location of the ischemic region, and the one or more therapy-monitoring parameters, the adjusting including adjusting one or more global pacing parameters of the chronic pacing therapy to reduce overall workload on the heart in response to the occurrence of the ischemic event and adjusting one or more regional pacing parameters of the post-ischemia pacing therapy to provide pre-excitation of the ischemic region to reduce stress and workload of the ischemic region in response to the occurrence of the ischemic event.

16. The method of claim 15, further comprising delivering the post-ischemia therapy to the ischemic region.

17. The method of claim 16, wherein sensing the one or more physiologic signals comprises sensing one or more physiologic signals using a plurality of electrodes, and locating the ischemic region comprises identifying at least one electrode of the plurality of electrodes in or closest to the ischemic region.

18. The method of claim 15, wherein producing the one or more therapy-monitoring parameters comprises:
    producing at least one chronic therapy-monitoring parameter from at least one chronic therapy-monitoring signal of the one or more therapy-monitoring signals, the at least one chronic therapy-monitoring parameter indicative of effectiveness of the chronic pacing therapy; and
    producing at least one post-ischemia therapy-monitoring parameter from at least one post-ischemia therapy-monitoring signal of the one or more therapy-monitoring signals, the at least one post-ischemia therapy-monitoring parameter indicative of effectiveness of the post-ischemia therapy, and wherein adjusting the delivery of the chronic pacing therapy and the delivery of the post-ischemia therapy comprises:
  adjusting the delivery of the chronic pacing therapy based on the detected ischemic state and the at least one chronic therapy-monitoring parameter; and
  adjusting the delivery of the post-ischemia therapy based on the detected ischemic state and the at least one post-ischemia therapy-monitoring parameter.

19. The method of claim 15, wherein delivering the chronic pacing therapy comprises delivering cardiac pacing pulses to a plurality of regions in the heart.

20. The method of claim 19, wherein initiating the delivery of the post-ischemia therapy comprises initiating a delivery of a neural stimulation therapy.

21. The method of claim 19, wherein initiating the delivery of the post-ischemia therapy comprises initiating a delivery of a drug therapy.

22. The method of claim 19, wherein initiating the delivery of the post-ischemia therapy comprises initiating a delivery of one or more biological substances.

23. The method of claim 19, wherein initiating the delivery of the post-ischemia therapy comprises initiating the delivery of the post-ischemia therapy by adjusting one or more pacing parameters of the chronic pacing therapy, and wherein the chronic pacing therapy comprises delivering the cardiac pacing pulses in an atrial tracking mode.

24. The method of claim 23, wherein adjusting the one or more pacing parameters of the chronic pacing therapy comprises shortening at least one atrioventricular delay associated with the ischemic region.

25. The method of claim 24, wherein adjusting the one or more pacing parameters comprises lowering a lower rate limit in response to the occurrence of the ischemic event.

* * * * *

UNITED STATES PATENT AND TRADEMARK OFFICE
CERTIFICATE OF CORRECTION

PATENT NO.       : 7,668,594 B2                              Page 1 of 1
APPLICATION NO. : 11/207251
DATED            : February 23, 2010
INVENTOR(S)      : Brockway et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 780 days.

Signed and Sealed this

Twenty-eighth Day of December, 2010

David J. Kappos
*Director of the United States Patent and Trademark Office*